(12) United States Patent
Fujii et al.

(10) Patent No.: US 9,176,074 B2
(45) Date of Patent: Nov. 3, 2015

(54) PATTERN INSPECTION METHOD AND PATTERN INSPECTION APPARATUS

(71) Applicant: KABUSHIKI KAISHA TOSHIBA, Minato-ku (JP)

(72) Inventors: Takayoshi Fujii, Yokohama (JP); Kiminori Yoshino, Yokkaichi (JP); Makoto Kaneko, Yokkaichi (JP); Yusaku Konno, Yokohama (JP); Yusuke Iida, Yokkaichi (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 138 days.

(21) Appl. No.: 14/018,739

(22) Filed: Sep. 5, 2013

(65) Prior Publication Data
US 2014/0212023 A1    Jul. 31, 2014

Related U.S. Application Data

(60) Provisional application No. 61/757,339, filed on Jan. 28, 2013.

(51) Int. Cl.
| | |
|---|---|
| *G06K 9/00* | (2006.01) |
| *G01N 21/956* | (2006.01) |
| *G06T 7/00* | (2006.01) |
| *G01R 31/311* | (2006.01) |

(52) U.S. Cl.
CPC ........ *G01N 21/95607* (2013.01); *G06T 7/0004* (2013.01); *G01R 31/311* (2013.01); *G06T 2207/10061* (2013.01); *G06T 2207/30148* (2013.01)

(58) Field of Classification Search
None
See application file for complete search history.

(56) References Cited

U.S. PATENT DOCUMENTS

| | | | |
|---|---|---|---|
| 6,226,079 B1 | 5/2001 | Takeda et al. | |
| 6,337,488 B1 * | 1/2002 | Okawauchi | 250/559.05 |
| 7,729,528 B2 * | 6/2010 | O'Dell et al. | 382/149 |
| 8,269,969 B2 * | 9/2012 | Hayano | 356/369 |
| 2008/0040064 A1 * | 2/2008 | Ishikawa | 702/108 |
| 2011/0221885 A1 | 9/2011 | Suzuki et al. | |
| 2012/0242985 A1 | 9/2012 | Watabiki et al. | |
| 2012/0243770 A1 | 9/2012 | Kaneko et al. | |

FOREIGN PATENT DOCUMENTS

| | | |
|---|---|---|
| JP | 11-101624 | 4/1999 |
| JP | 2009-43960 | 2/2009 |
| JP | 2010-151802 | 7/2010 |
| JP | 2010-249552 | 11/2010 |
| JP | 2012-202862 | 10/2012 |
| JP | 2012-202866 | 10/2012 |

* cited by examiner

*Primary Examiner* — Daniel Mariam
(74) *Attorney, Agent, or Firm* — Oblon, McClelland, Maier & Neustadt, L.L.P.

(57) ABSTRACT

In accordance with an embodiment, a pattern inspection method includes applying a light to a substrate including an inspection target pattern in a plurality of optical conditions, detecting a reflected light from the substrate to acquire a pattern image for each of the optical conditions, outputting a gray value difference between the pattern image and a reference image for each of the optical conditions, and specifying a position of the defect in a stacking direction of the stacked film from a relation of the obtained gray value difference between the optical conditions. The pattern is formed by a stacked film, the optical conditions includes at least a first optical condition for detection of a defect on a surface of the stacked film.

20 Claims, 19 Drawing Sheets

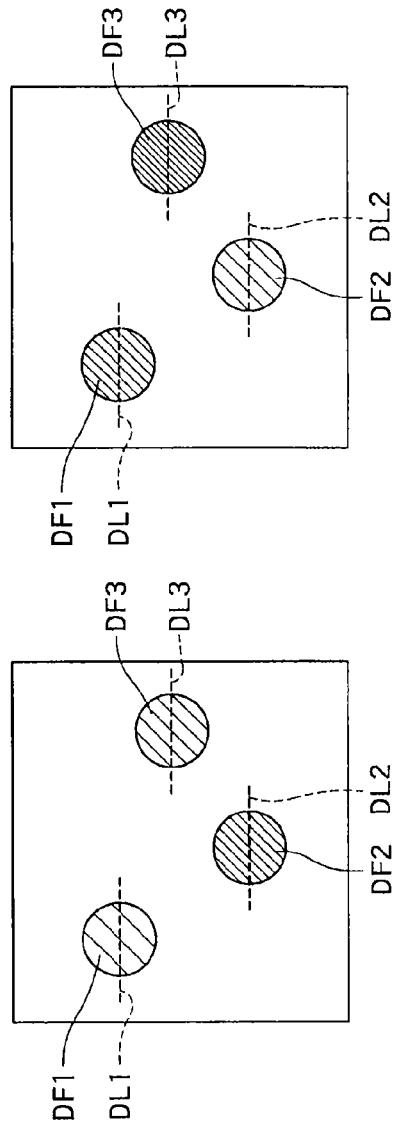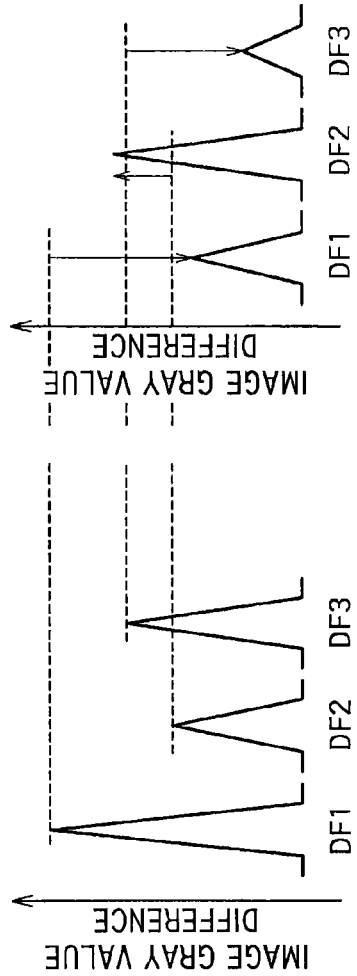

PATTERN INSPECTION METHOD AND PATTERN INSPECTION APPARATUS

CROSS REFERENCE TO RELATED APPLICATIONS

This application is based upon and claims the benefit of U.S. provisional Application No. 61/757,339, filed on Jan. 28, 2013, the entire contents of which are incorporated herein by reference.

FIELD

Embodiments described herein relate generally to a pattern inspection method and a pattern inspection apparatus.

BACKGROUND

In the fields of semiconductor devices, flat panel displays, and micro electro mechanical systems (MEMS), and so on, a structure having micro patterns formed on its surface (hereinafter referred to as a "microstructure") is manufactured, for example, by lithographic technology.

An optical inspection apparatus is used for the inspection of such a microstructure. The conventional optical inspection apparatus applies a light to an inspection target pattern formed on a substrate such as a wafer from, for example, a laser light source or a lamp light source, detects a reflected light from the pattern by a detector, and compares the signal intensity of the detected light by, for example, die-to-die comparison, thereby conducting a defect inspection. Recently, patterns having high aspect ratios have been produced due to advanced miniaturization and integration of the microstructures. For example, in a trench pattern having a high aspect ratio, defects can be generated at various positions in a depth direction. Therefore, when it is judged that there is a defect, a correct judgment of its position in the depth direction is required.

BRIEF DESCRIPTION OF THE DRAWINGS

In the accompanying drawings:

FIG. 2A and FIG. 2B show examples of gray value difference images between an inspection target pattern image and a reference image respectively obtained regarding two different optical conditions;

FIG. 3A and FIG. 3B respectively show gray value difference profiles for parts indicated in dashed line in FIG. 2A and FIG. 2B;

DETAILED DESCRIPTION

In accordance with an embodiment, a pattern inspection method includes applying a light to a substrate including an inspection target pattern in a plurality of optical conditions, detecting a reflected light from the substrate to acquire a pattern image for each of the optical conditions, outputting a gray value difference between the pattern image and a reference image for each of the optical conditions, and specifying a position of the defect in a stacking direction of the stacked film from a relation of the obtained gray value difference between the optical conditions. The pattern is formed by a stacked film, the optical conditions includes at least a first optical condition for detection of a defect on a surface of the stacked film.

Embodiments will now be explained with reference to the accompanying drawings. Like components are provided with like reference signs throughout the drawings and repeated descriptions thereof are appropriately omitted. The gray value difference of images is expressed by the width of a hatched space.

(1) Pattern Inspection Apparatus
(A) Apparatus Configuration

Figure 1:
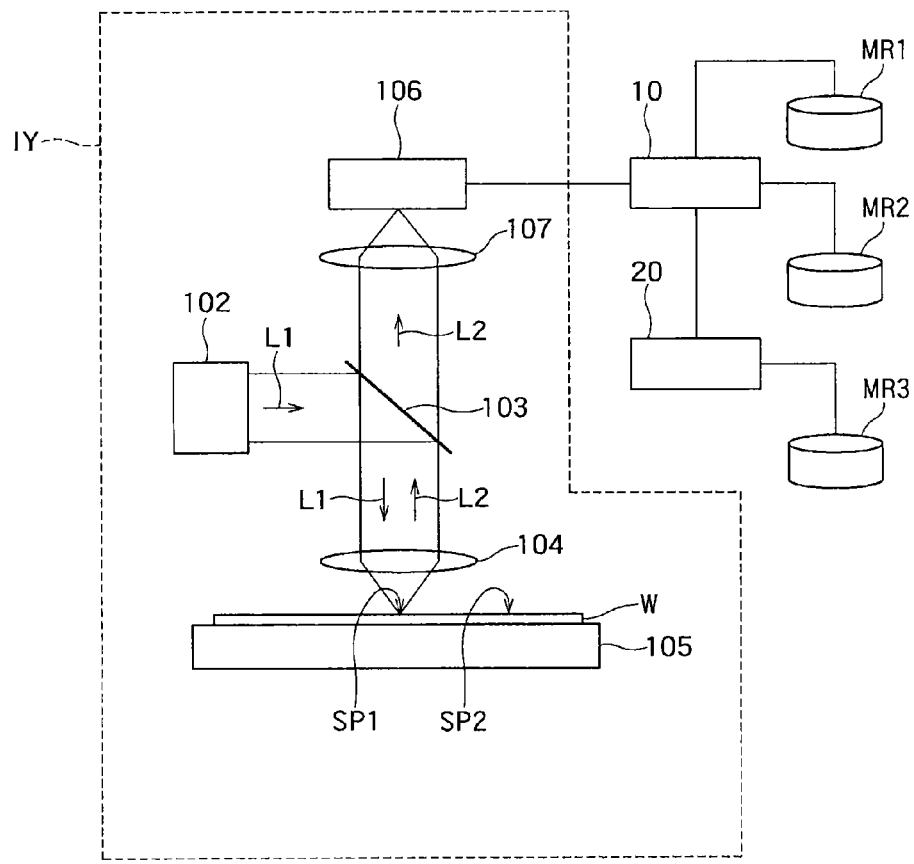
FIG. 1 is a block diagram showing the schematic structure of a pattern inspection apparatus according to one embodiment.

FIG. 1 is a block diagram showing the schematic structure of a pattern inspection apparatus according to one embodiment. The pattern inspection apparatus shown in FIG. 1 includes an imaging unit IY, a gray value difference output unit 10, and a depth direction position specifying unit 20. Two memories MR1 and MR2 are connected to the gray value difference output unit 10, and a memory MR3 is connected to the depth direction position specifying unit 20.

The imaging unit IY is provided with a light source 102, a beam splitter 103, a mount 105, and a detector 106. On an optical path, an objective lens 104 and an imaging lens 107 are provided. In the present embodiment, the light source 102, the beam splitter 103, and the objective lens 104 correspond to, for example, an illumination unit.

The light source 102 emits a light L1 of a lamp light source, the wavelength of the light L1 ranging from an ultraviolet wavelength to a visible wavelength, of about 250 nm to about 600 nm. The light source is not limited thereto, and a laser light, for example, can be used instead.

The beam splitter 103 reflects the light L1 emitted from the light source 102, and guides the light to a wafer W including an inspection target pattern P1 in which a stack film is formed, and then transmits a reflected light L2 from the pattern P1 and guides the reflected light L2 to the detector 106. In the present embodiment, the wafer W corresponds to, for example, a substrate.

The wafer W is mounted on and held by the mount 105, and the mount 105 changes the position of the held wafer W. The mount 105 can be, for example, an XY table having an unshown electrostatic chuck.

The detector 106 includes, for example, a charge coupled device (CCD) or a photomultiplier, and photoelectrically converts a light of an image formed on a light-receiving surface, and outputs the photoelectrically converted light as a signal.

The objective lens 104 focuses the light L1 reflected by the beam splitter 103 onto the inspection target pattern P1 laid on the wafer W. The imaging lens 107 focuses the reflected light L2 which has passed through the beam splitter 103 onto the light-receiving surface of the detector 106. That is, the imaging lens 107 forms an optical image of the inspection target on the light-receiving surface of the detector 106. In the present embodiment, the imaging lens and the detector 106 correspond to, for example, a detection unit.

The signal from the detector 106 is sent to the gray value difference output unit 10, and temporarily stored in the memory MR1. Data on a reference image is stored in the memory MR2. When a die-to-die comparison or cell-to-cell comparison is used, an image of a pattern P2 can be used as the reference image. The pattern P2 is formed by a pattern having the same design as the pattern P1, and located in a region different from the region where the pattern P1 is formed within the surface region of the wafer W. In this case, the image of the pattern P2 is stored in the memory MR2 for each optical condition. In the cases below, the die-to-die comparison or cell-to-cell comparison is mainly described by way of example.

The reference image is not limited to the above-mentioned images in the cases of the die-to-die comparison or cell-to-cell comparison. For example, it is also possible to use an image obtained regarding a reference pattern which has been previously ascertained to be nondefective, or an image obtained by a simulation (die-to-database comparison).

The gray value difference output unit 10 calculates, for each optical condition, a gray value difference between the image data stored in the memory MR1 and the reference image data stored in the memory MR2, and sends the gray value difference to the depth direction position specifying unit 20.

The depth direction position specifying unit 20 finds the relation between the optical conditions regarding the data on the gray value difference sent from the gray value difference output unit 10, and specifies, from the obtained relation, the position of a defect, that is, the depth of a defect in a direction perpendicular to the wafer W, that is, in the stacking direction of a stacked film stacked on the wafer W.

(B) Operation

The operation of the pattern inspection apparatus shown in FIG. 1 is described.

First, optical conditions of the imaging unit IY are set. As the optical conditions, a plurality of optical conditions including at least an optical condition for detection of a defect on the surface of the stacked film are set. In the present embodiment, an optical condition 1 for detection of a defect on the surface of the stacked film, and an optical condition 2 for detection of a defect within the stacked film are set. A more specific method of setting each of the optical conditions will be described later. In the present embodiment, the optical conditions 1 and 2 respectively correspond to, for example, first and second optical conditions.

The optical condition 1 is then set, and the wafer W is mounted on and held by the mount 105 using an unshown conveyer. A light L1 is then emitted from the light source 102. The light L1 emitted from the light source 102 is reflected by the beam splitter 103, and guided to the wafer W. In this case, the light L1 is focused by the objective lens 104, and applied to the inspection target pattern P1.

The reflected light L2 from the pattern P1 then passes through the beam splitter 103, and is then focused on the light-receiving surface of the detector 106 by the imaging lens 107. That is, an optical image of the pattern P1 is formed on the light-receiving surface of the detector 106. The light of the optical image formed on the light-receiving surface of the detector 106 is photoelectrically converted, and an image signal of the pattern P1 is thereby obtained. The obtained image signal is stored in the memory MR1 via the gray value difference output unit 10.

The optical condition 2 is then set, the imaging unit IY is operated by the procedure described above, and an image signal of the pattern P1 is obtained. The obtained image signal is stored in the memory MR1 via the gray value difference output unit 10.

The mount 105 is then moved by an unshown drive unit to move the wafer W so that the pattern P2 is brought into the field of view. At this position, image signals of the pattern P2 are acquired regarding the optical conditions 1 and 2 by the procedure described above, and stored in the memory MR1 via the gray value difference output unit 10.

The gray value difference output unit 10 then draws the image data for the pattern P1 from the memory MR1 in each of the optical conditions, draws the reference image data from the memory MR2, and calculates a gray value difference. In the present embodiment, as the reference image is the image data for the pattern P2, the gray value difference output unit 10 calculates a gray value difference between the patterns P1 and P2.

Examples of the gray value difference images thus obtained are shown in FIG. 2A and FIG. 2B. FIG. 2A shows the gray value difference image obtained regarding the optical condition 1, and FIG. 2B shows the gray value difference image obtained regarding the optical condition 2. Defects DF1 to DF3 are seen in each of the images. Here, assumption is made that the size of the defect DF1 is larger than the sizes of the defects DF2 and DF3.

FIG. 3A and FIG. 3B respectively show gray value difference profiles for parts DL1 to DL3 indicated in dashed line in FIG. 2A and FIG. 2B.

Finally, the depth direction position specifying unit 20 specifies the position of the defect in a depth direction from the relation of the gray value difference between the optical conditions. There are two specifying methods: (a) a method of specifying whether the defect is present on the surface or present within the stacked film by the magnitude relation of the gray value difference; (b) a method of specifying a specific depth by referring to a data table regarding the ratio of the gray value difference.

(a) Specification of defect position by gray value difference magnitude relation The depth direction position specifying unit 20 judges whether the defects DF2 and DF3 are the defects on the surface of the stacked film or the defects within the stacked film by the magnitude relation of the gray value difference between the optical conditions. Specifically, when the light L1 is absorbed by the stacked film in the optical condition 1 and the light L1 passes through the stacked film in the optical condition 2, the gray value difference in the optical condition 2 is greater than the gray value difference in the optical condition 1 regarding the defect DF2 when FIG. 3A and FIG. 3B are compared with each other. Therefore, the defect DF2 is determined to be the defect within the stacked film. Regarding the defect DF3, the gray value difference in the optical condition 2 is smaller than the gray value difference in the optical condition 1, so that the defect DF3 is determined to be the defect on the surface of the stacked film.

In another determination method that uses a threshold, a great difference of gray value is detected from the defect DF1 present on the surface of the stacked film because of its large size, so that the defect DF1 may be erroneously determined to be the defect within the stacked film. As the present embodiment is based on the magnitude relation of the gray value difference between the optical conditions, and the gray value difference in the optical condition 2 is smaller than the gray value difference in the optical condition 1, so that even a defect having a large size can be correctly determined to be the defect on the surface.

(b) Specification of Defect Position Referring to Data Table Regarding Gray Value Difference Ratio The method of specifying a defect position by referring to the data table regarding the ratio of the gray value difference is described with reference to FIG. 4A to FIG. 5B.

Figure 4A:
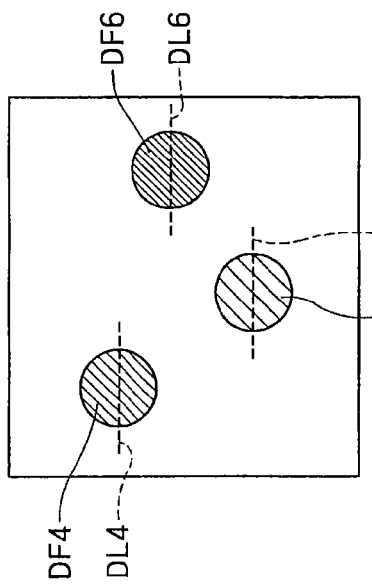
FIG. 4A and FIG. 4B show other examples of gray value difference images between an inspection target pattern image and a reference image respectively obtained regarding the two different optical conditions.
Figure 4B:
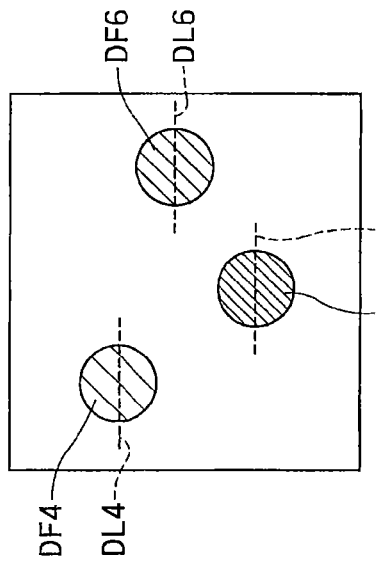

FIG. 4A and FIG. 4B show other examples of gray value difference images obtained by the procedure described above. FIG. 4A represents a gray value difference image obtained regarding the optical condition 1, and FIG. 4B shows the gray value difference image obtained regarding the optical condition 2. Defects DF4 to DF6 are seen in each of the images.

Figure 5A:
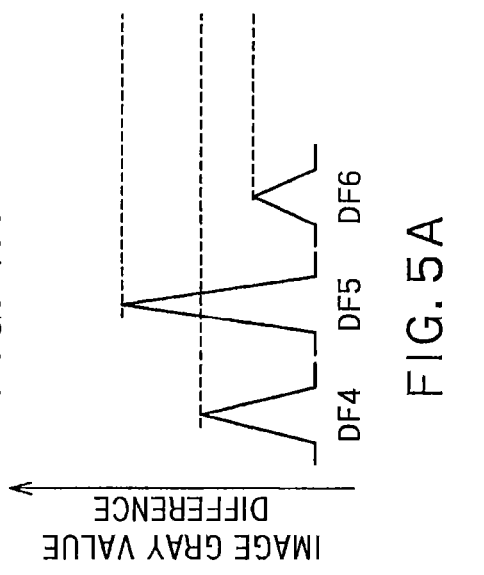
FIG. 5A and FIG. 5B respectively show gray value difference profiles for parts DL1 to DL3 indicated in dashed line in FIG. 4A and FIG. 4B.
Figure 5B:
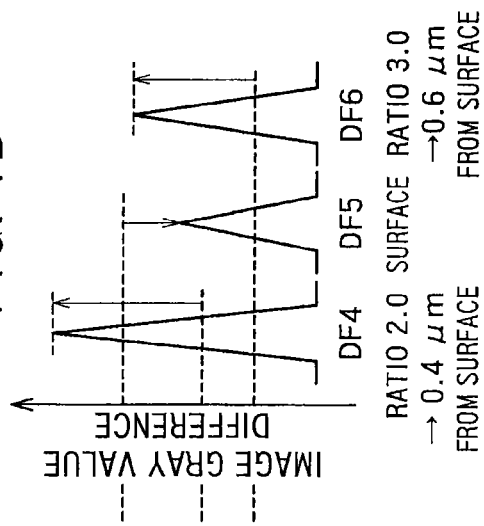

FIG. 5A and FIG. 5B respectively show gray value difference profiles for parts DL4 to DL6 indicated in dashed line in FIG. 4A and FIG. 4B.

In the examples shown in FIG. 4A to FIG. 5B, the relation between the position of the defect in the depth direction and the rate of a change between the gray value difference in different optical conditions is checked in advance, and stored as the data table in, for example, the memory M3 in FIG. 1. In the data table, by way of example, the ratio of the gray value difference in the optical condition 2 to the gray value difference in the optical condition 1 is 1.5 times, 2.0 times, 3.0 times, 5.0 times, and 10.0 times when the position of the defect in the depth direction is, for example, 0.2 μm, 0.4 μm, 0.6 μm, 0.8 μm, 1.0 μm from the surface.

The depth direction position specifying unit 20 calculates the ratio of the pixel gray value difference between the optical conditions for each defect, and specifies the position in the depth direction corresponding to the obtained ratio by referring to the data table. For example, as the ratio of the gray value difference is calculated at 3.0 times for the defect DF6 in FIG. 4A and FIG. 4B, the depth direction position specifying unit 20 determines that the defect DF6 is located at a position of 0.6 μm from the surface of the stacked film.

Thus, the data table regarding the position of the defect in the depth direction and the ratio of the gray value difference between the optical conditions is prepared. When the ratio of the pixel gray value difference between the optical conditions found for each defect is compared with the data table, the position of the defect in the depth direction can be quantitatively calculated.

(C) Examples of Different Optical Conditions

Figure 6A:
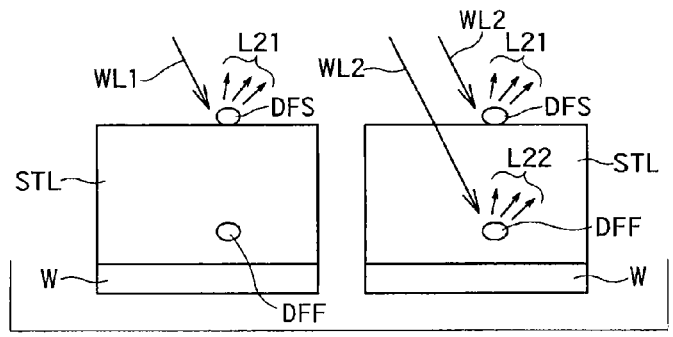
FIG. 6A to FIG. 6C are diagrams showing specific examples of different optical conditions.
Figure 6B:
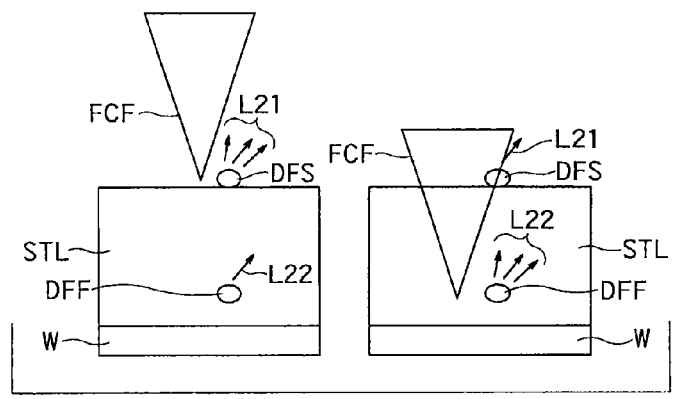
Figure 6C:
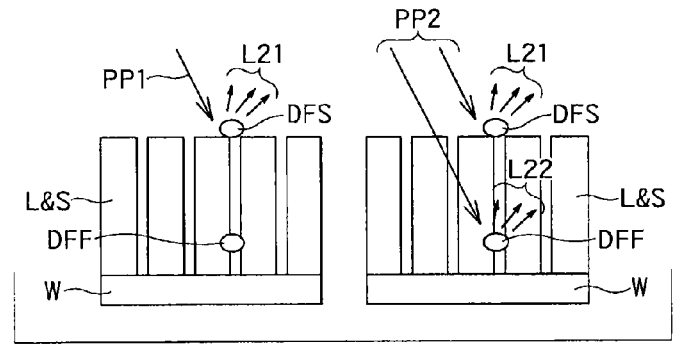

FIG. 6A to FIG. 6C are diagrams showing specific examples of different optical conditions.

First, in the example shown in FIG. 6A, different wavelengths are used to provide a plurality of optical conditions. Specifically, a light having a wavelength WL1 absorbed by a stacked film STL is applied in the optical condition 1, and a light having a wavelength WL2 which passes through a stacked film STL is applied in the optical condition 2. Accordingly, a reflected light L21 is generated from a surface defect DFS in both the optical conditions, whereas a reflected light L22 is generated from a defect DFF within the stacked film STL in the optical condition 2 alone.

FIG. 6B shows an example in which different optical conditions are obtained by different focus positions. Specifically, a focus FCS is adjusted to the surface of the stacked film STL in the optical condition 1, and a focus FCS is adjusted within the stacked film STL in the optical condition 2. Accordingly, the amount of the reflected light L21 generated from the surface defect DFS is greater in the optical condition 1 than in the optical condition 2. On the other hand, the amount of the reflected light L22 generated from the defect DFF within the stacked film STL is greater in the optical condition 2 than in the optical condition 1.

FIG. 6C shows an example in which different optical conditions are obtained by different polarized lights. Specifically, when an inspection target pattern is a line-and-space pattern, the line-and-space pattern is illuminated, for example, by a linearly polarized light PP1 which does not pass through the line-and-space pattern and which is parallel to the lines in the optical condition 1. The line-and-space pattern is illuminated, for example, by a linearly polarized light PP2 which passes through the line-and-space pattern to its bottom and which is perpendicular to the lines in the optical condition 2. Accordingly, the reflected light L21 is generated from the surface defect DFS in both the optical conditions, whereas the reflected light L22 is generated from the defect DFF within a line-and-space pattern in the optical condition 2 alone.

(D) Configuration Example of Optical System to Provide Each Optical Condition (i) Wavelength FIG. 7A to FIG. 7D show configuration examples of imaging units to provide different optical conditions using different wavelengths.

Figure 7A:
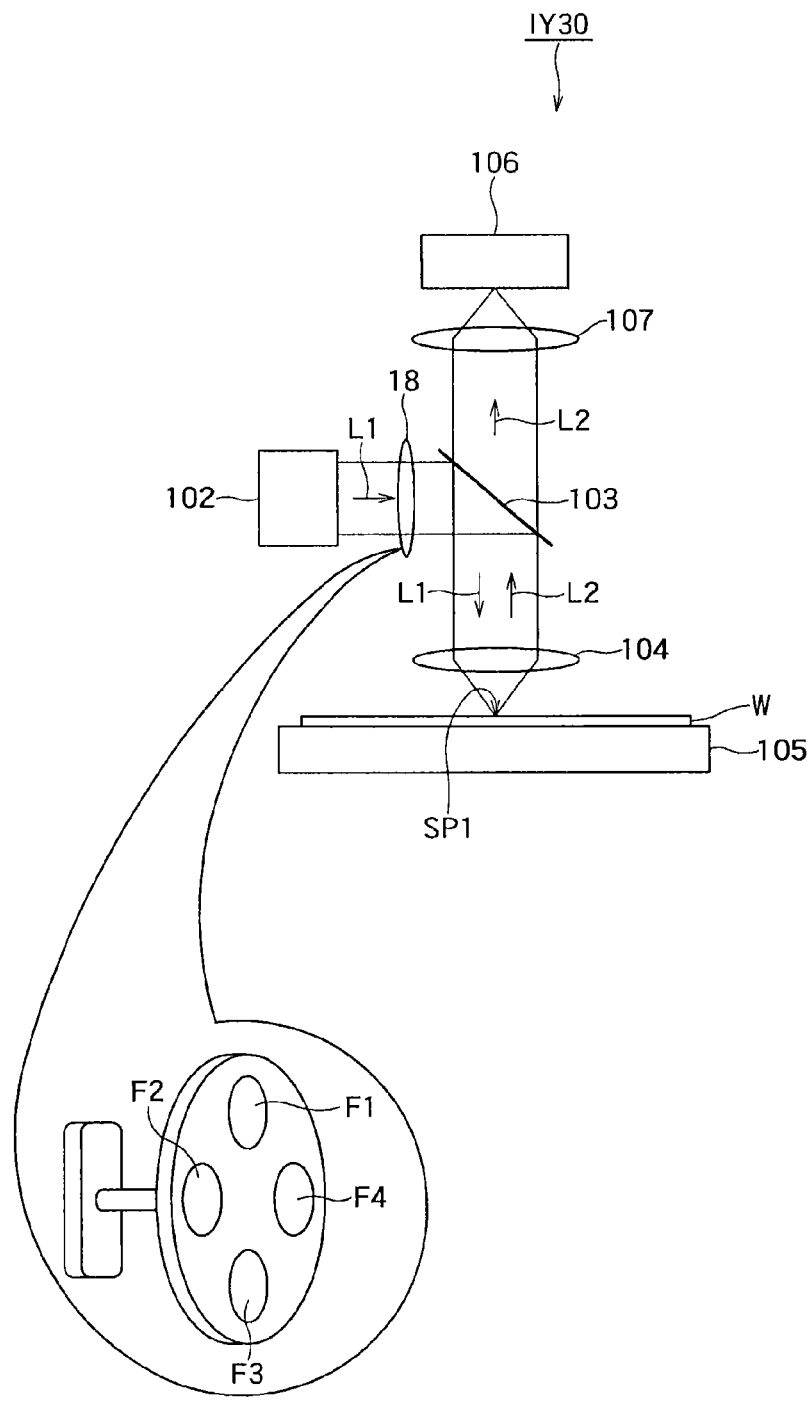
FIG. 7A to FIG. 7D show configuration examples of imaging units to provide different optical conditions using different wavelengths.

An imaging unit IY30 shown in FIG. 7A includes, as the light source 102, a single white light source which generates a broad light, and further includes a filter switch 18 in addition to the configuration of the imaging unit IY in FIG. 1. The filter switch 18 includes a plurality of filters different in wavelength (F1 to F4 in the example in FIG. 7A), and is disposed between the light source 102 and the beam splitter 103 to illuminate a light having a desired wavelength component out of the light from the light source 102. In the present embodiment, the filters F1 to F4 and the filter switch 18 respectively correspond to, for example, wavelength filters and a switch.

Figure 7B:
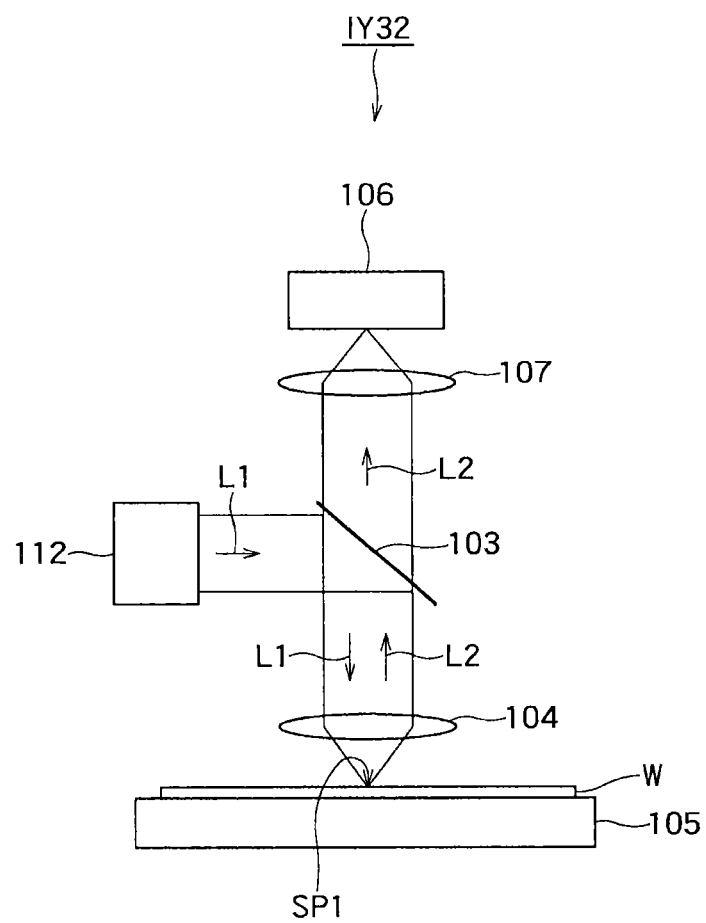

An imaging unit IY32 shown in FIG. 7B includes, instead of the light source 102 shown in FIG. 1, a light source 112 which emits lights having different wavelengths. A light source variable in wavelength or a plurality of light sources different in wavelength may be used as the light source 112.

Figure 7C:
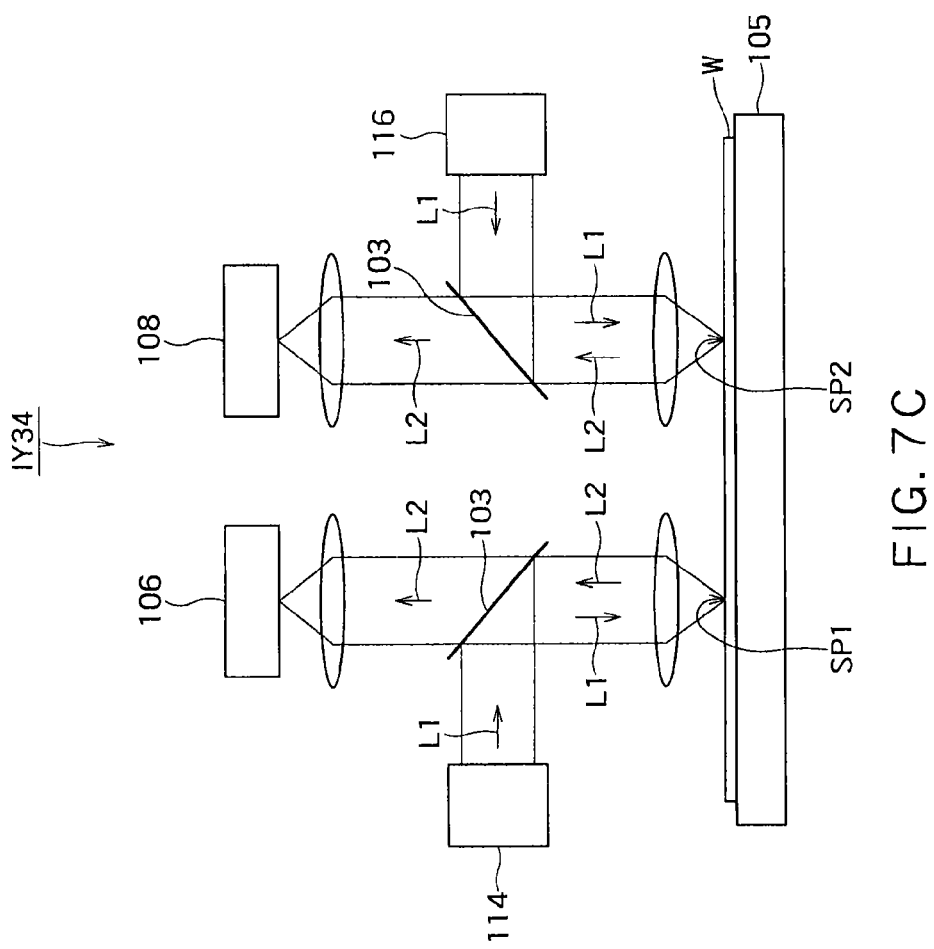

An imaging unit IY34 shown in FIG. 7C includes two light sources 114 and 116 which emit lights having different wavelengths, and includes two illumination optical systems and imaging optical systems and two detectors 106 and 108 that are provided to correspond to the two light sources.

Figure 7D:
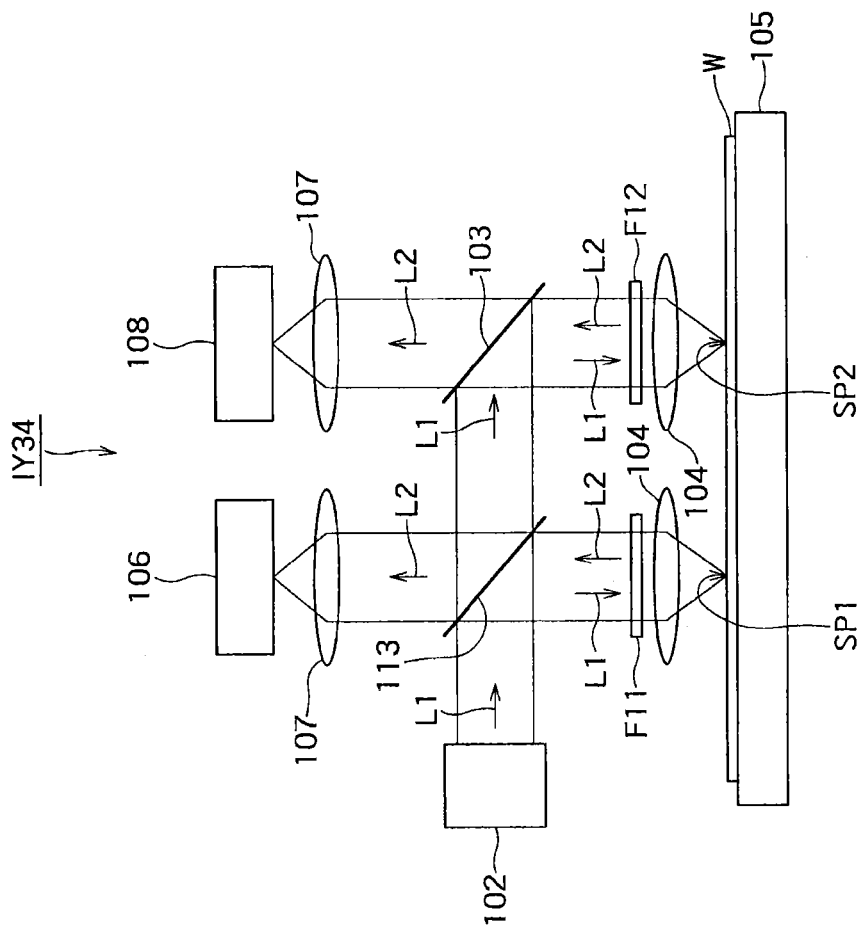

The imaging unit IY34 shown in FIG. 7D includes a beam splitter 113 which splits the light L1 from the single light source 102 into two optical paths, and two wavelength filters F11 and F12 for transmitting lights having different wavelengths, two illumination optical systems and imaging optical systems, and two detectors 106 and 108 that are provided to correspond to the two optical paths.

(ii) Focus Position

Figure 8A:
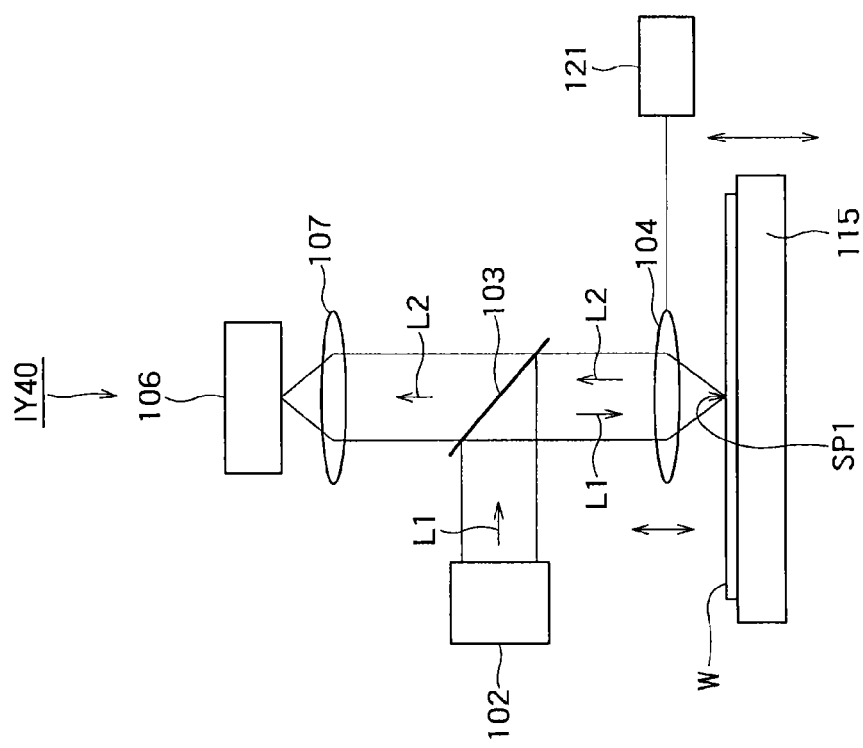
FIG. 8A to FIG. 8C show configuration examples of imaging units configured to provide different optical conditions using different focus positions.
Figure 8B:
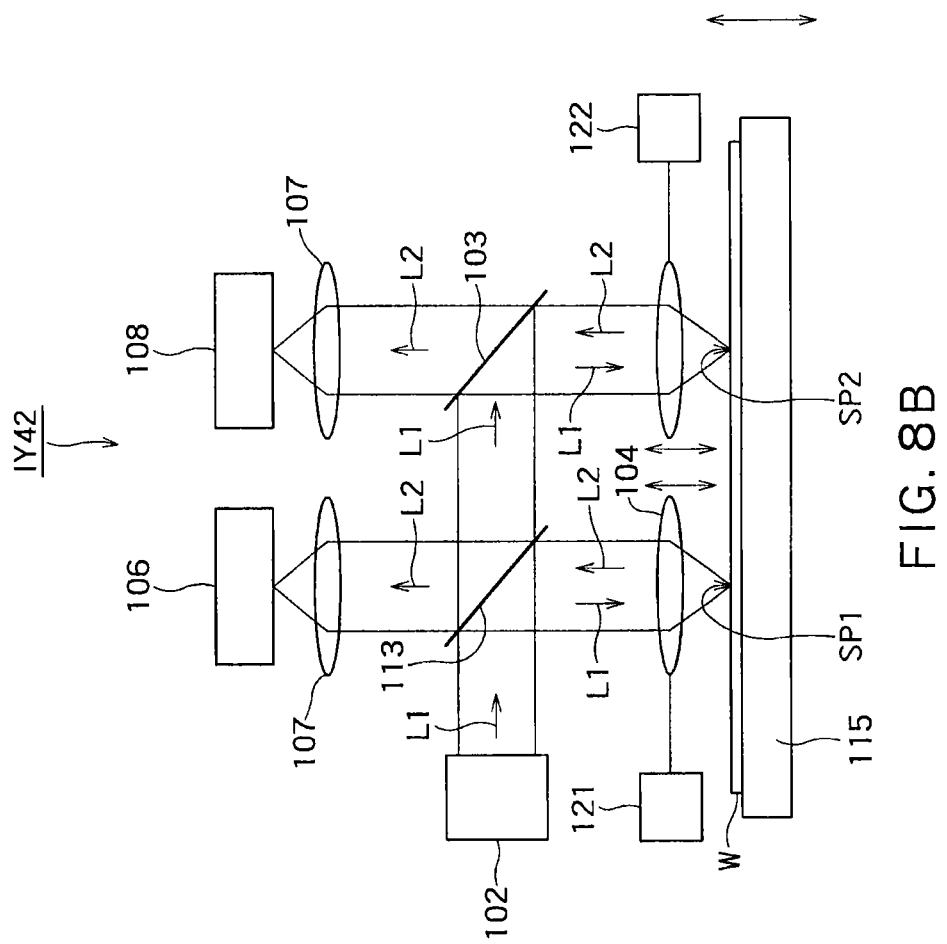
Figure 8C:
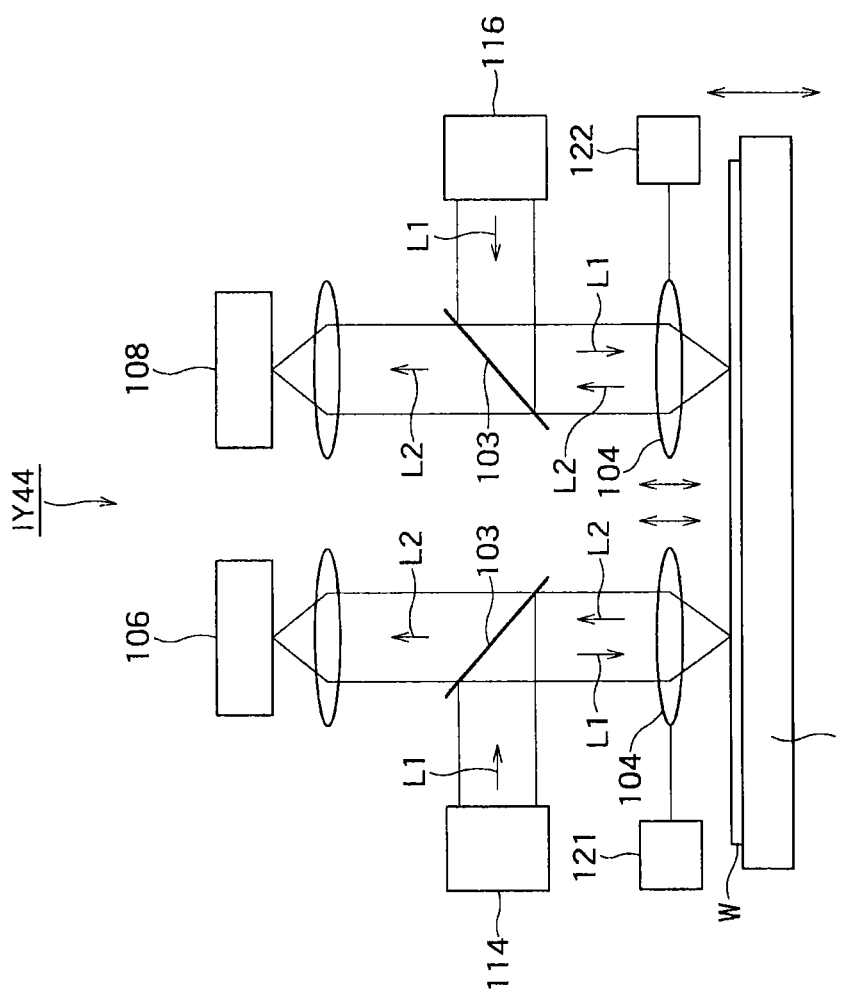

FIG. 8A to FIG. 8C show configuration examples of imaging units to provide different optical conditions using different focus positions.

An imaging unit IY40 shown in FIG. 8A includes, instead of the mount 105 shown in FIG. 1, a mount 115 capable of moving the wafer W in a vertical direction, and further includes an objective lens mover 121 capable of moving the position of the objective lens 104 in the vertical direction of the wafer W. When at least one of the mount 115 and the objective lens mover 121 is activated, the distance between the wafer W and the objective lens 104 varies, so that a plurality of optical conditions different in focus position can be obtained. In this example, the mount 115 and the objective lens mover 121 correspond to, for example, a focus position adjusting unit.

An imaging unit IY42 shown in FIG. 8B includes, in addition to the mount 115, the beam splitter 113 which splits the light L1 from the single light source 102 into two optical paths, and two illumination optical systems and imaging optical systems, two objective lens movers 121 and 122, and two detectors 106 and 108 that are provided to correspond to the two optical paths.

An imaging unit IY44 shown in FIG. 8C includes, in addition to the mount 115, two light sources 114 and 116, and two illumination optical systems and imaging optical systems, two objective lens movers 121 and 122, and two detectors 106 and 108 that are provided to correspond to the two light sources.

In the examples FIG. 8B and FIG. 8C, the mount 115 and the objective lens movers 121 and 122 correspond to, for example, the focus position adjusting unit.

(Iii) Polarization

FIG. 9A to FIG. 9D show configuration examples of imaging units to provide different optical conditions using different polarized lights. In this example, both the inspection target patterns P1 and P2 are line-and-space patterns (see FIG. 6C).

Figure 9A:
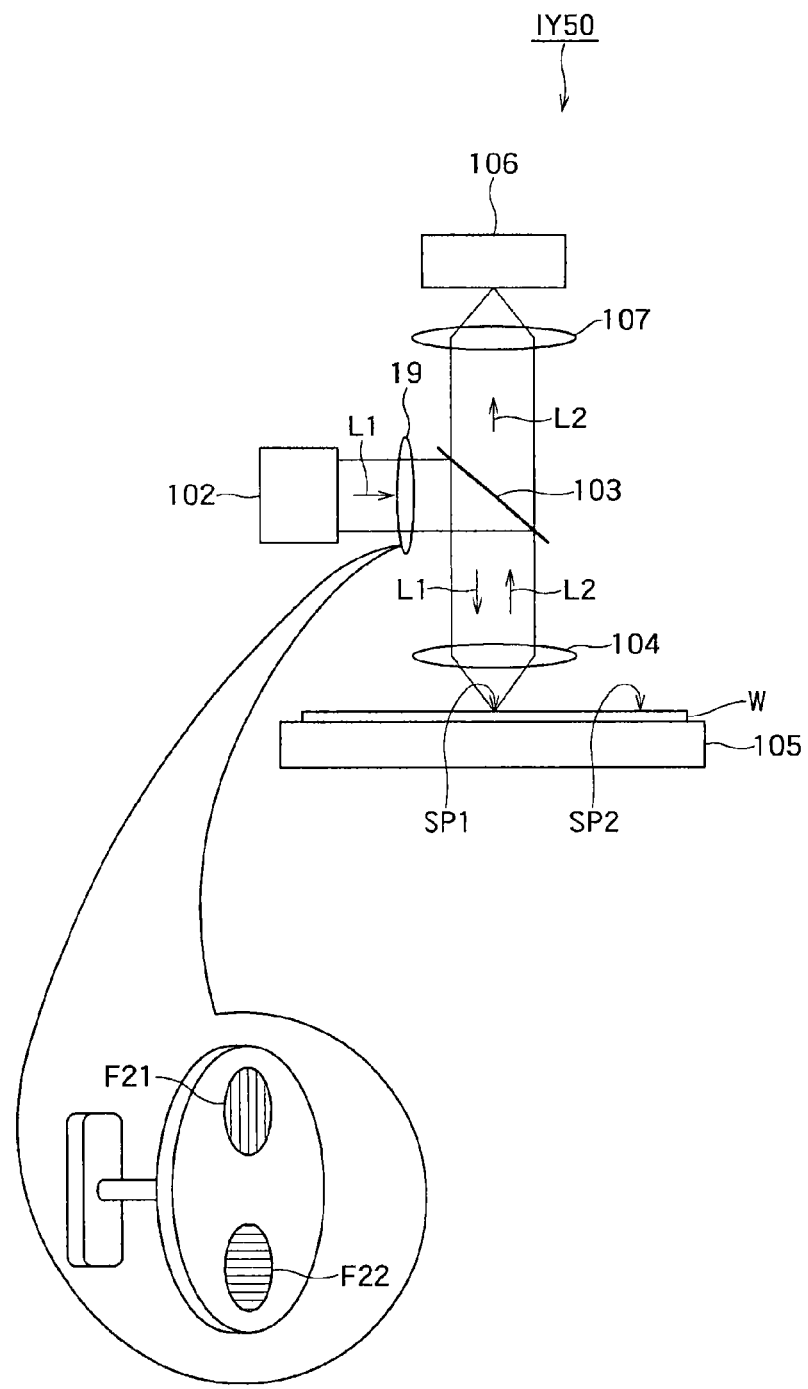
FIG. 9A to FIG. 9D show configuration examples of imaging units configured to provide different optical conditions using different polarized lights.

An imaging unit IY50 shown in FIG. 9A further includes a filter switch 19 in addition to the configuration of the imaging unit IY in FIG. 1. The filter switch 19 is disposed between the light source 102 and the beam splitter 103, and includes two different polarization filters F21 and F22. The filter switch 19 switches between the polarization filters F21 and F22 to selectively polarize the light L1 from the light source 102.

The polarization filter F21 illuminates the light L1 with linear polarization parallel to the lines of the patterns P1 and P2. The polarization filter F22 illuminates the light L1 with linear polarization that is perpendicular to the lines of the patterns P1 and P2. Thus, when the polarization filter F21 is selected, incident light does not pass through the stacked film, so that a reflected light is only generated from the defect on the surface. On the other hand, when the polarization filter F22 is selected, incident light passes through the stacked film, so that a reflected light is not only generated from the defect on the surface of the stacked film but also generated from the defect within the stacked film. In this example, the polarization filters F21 and F22 and the filter switch 19 correspond to, for example, a polarization unit.

Figure 9B:
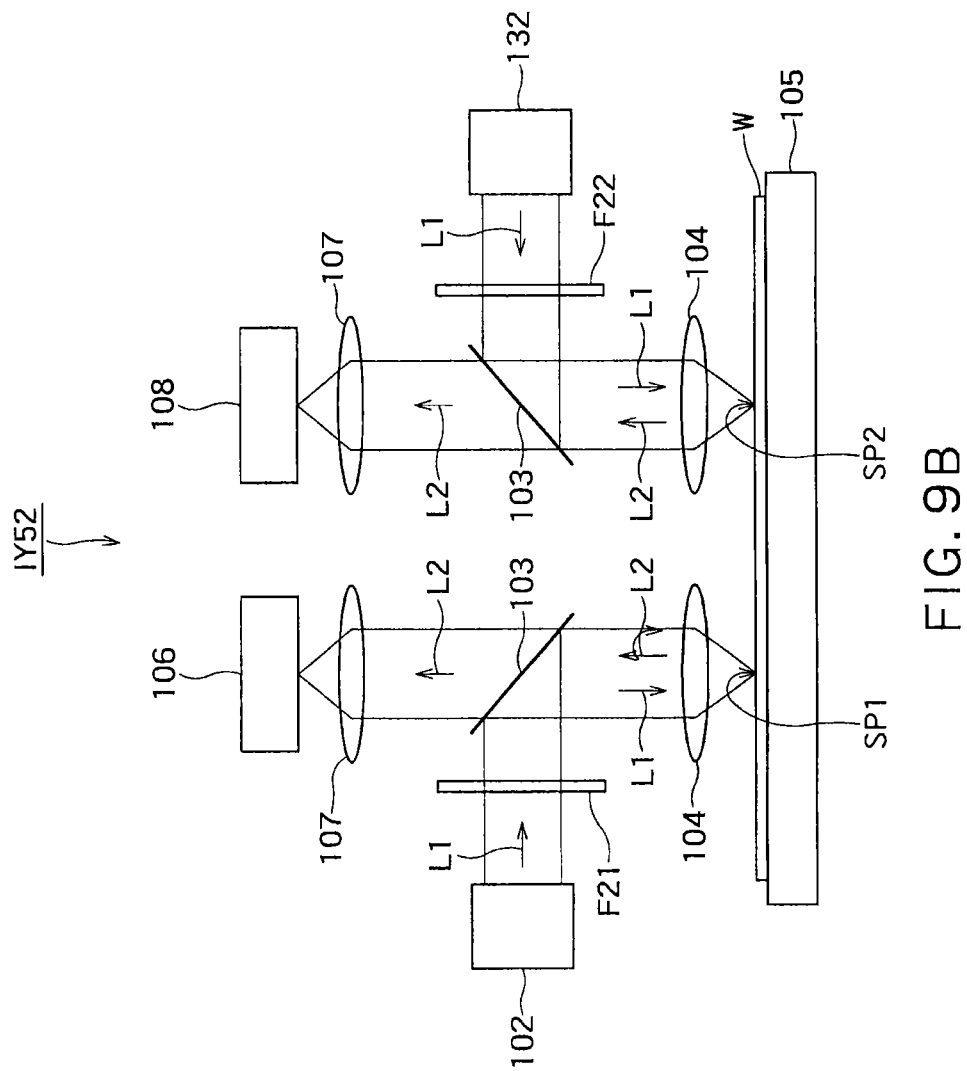

An imaging unit IY52 shown in FIG. 9B includes two light sources 102 and 132, and includes two illumination optical systems and imaging optical systems, two polarization filters F21 and F22, and two detectors 106 and 108 that are provided to correspond to the two light sources.

Figure 9C:
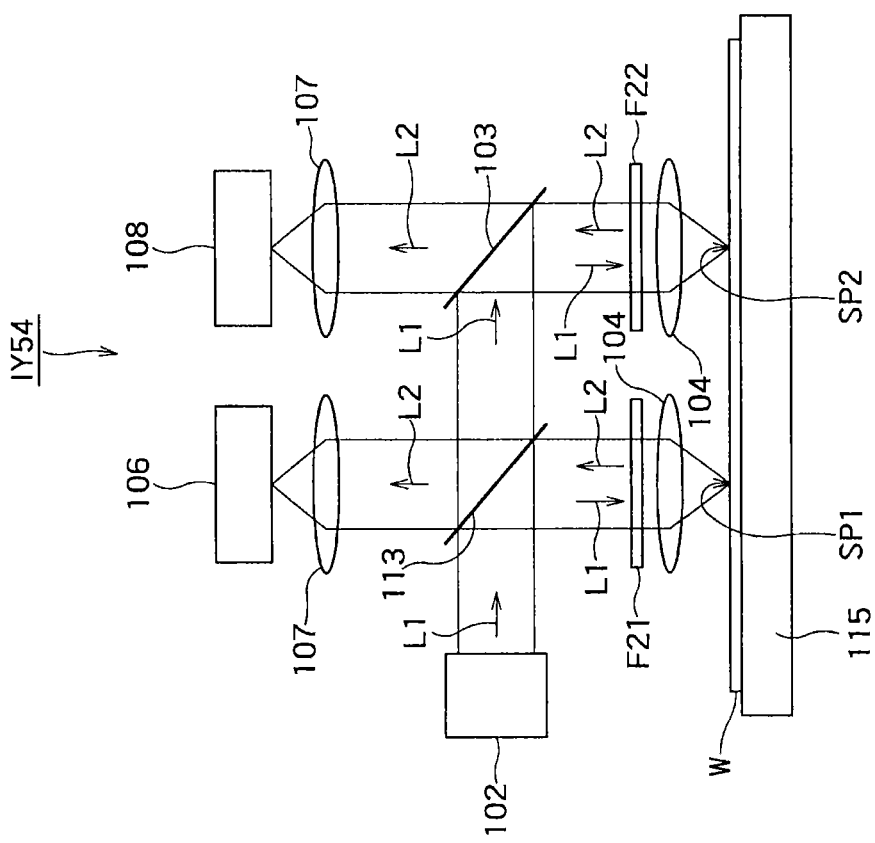

An imaging unit IY54 shown in FIG. 9C includes the beam splitter 113 which splits the light L1 from the single light source 102 into two optical paths, and two polarization filters F21 and F22, two illumination optical systems and imaging optical systems, and two detectors 106 and 108 that are provided to correspond to the two optical paths.

In the examples shown in FIG. 9B and FIG. 9C, the polarization filters F21 and F22 correspond to, for example, a polarization unit.

Figure 9D:
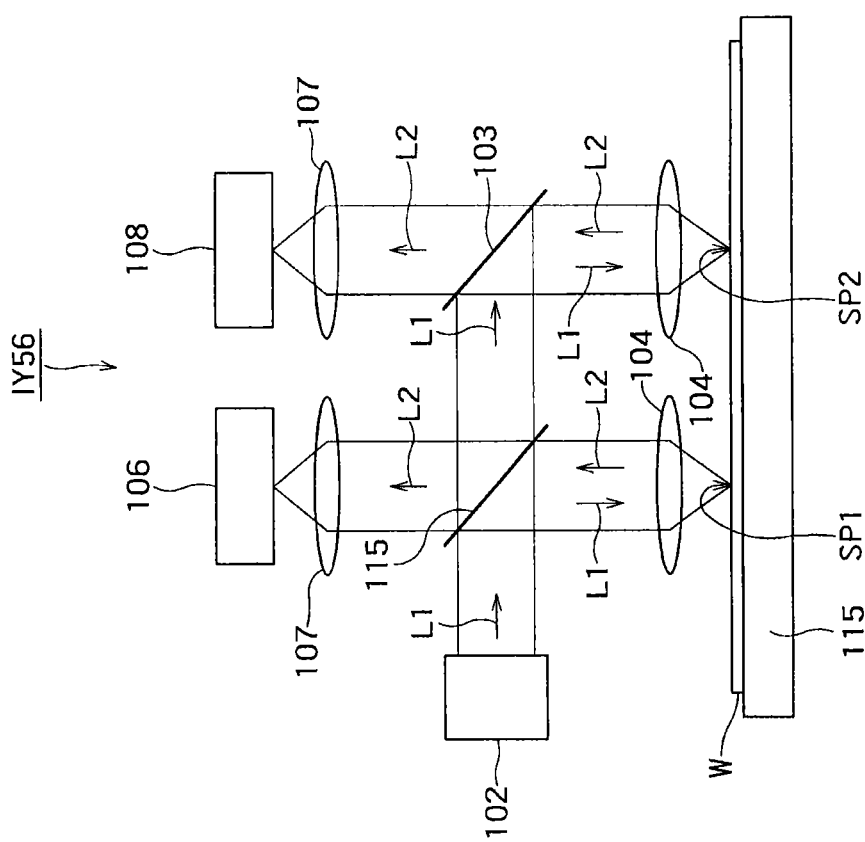

An imaging unit IY56 shown in FIG. 9D includes a polarizing beam splitter 115 which splits the light L1 from the single light source 102 into two optical paths and which performs parallel linear polarization and perpendicular linear polarization, and two illumination optical systems and imaging optical systems and two detectors 106 and 108 that are provided to correspond to the two optical paths. In this example, the polarizing beam splitter 115 corresponds to, for example, a polarization unit.

(E) Three or More Optical Conditions

According to the embodiments described above a pattern image is acquired in two optical conditions, however, this is not a limitation. The use of three or more optical conditions allows the position of the defect in the depth direction to be more accurately specified.

Figure 10:
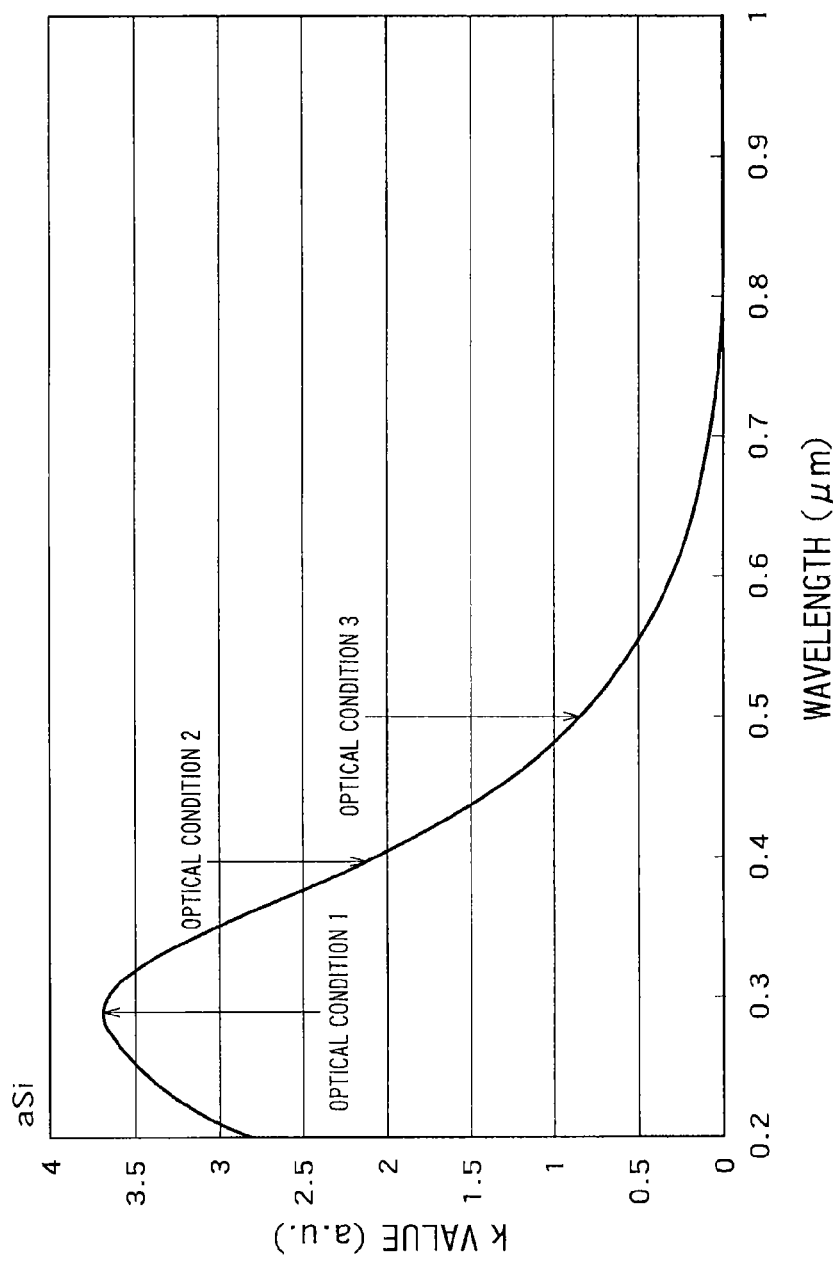
FIG. 10 is a graph showing the relation between the wavelength of an incident light and an absorption coefficient when a pattern is made of amorphous silicon.

FIG. 10 is a graph showing the relation between the wavelength of an incident light and an absorption coefficient k when a pattern is made of amorphous silicon. As apparent from FIG. 10, a sharp curve is drawn between about 0.3 μm and about 0.5 μm. Accordingly, if, for example, three optical conditions 1 to 3 at wavelengths of 0.3 μm, 0.4 μm, and 0.5 μm are provided, the positions of the defect in the depth direction corresponding to the respective k values can be specified. In the present embodiment, the optical conditions 2 and 3 correspond to, for example, a second optical condition.

Figure 11:
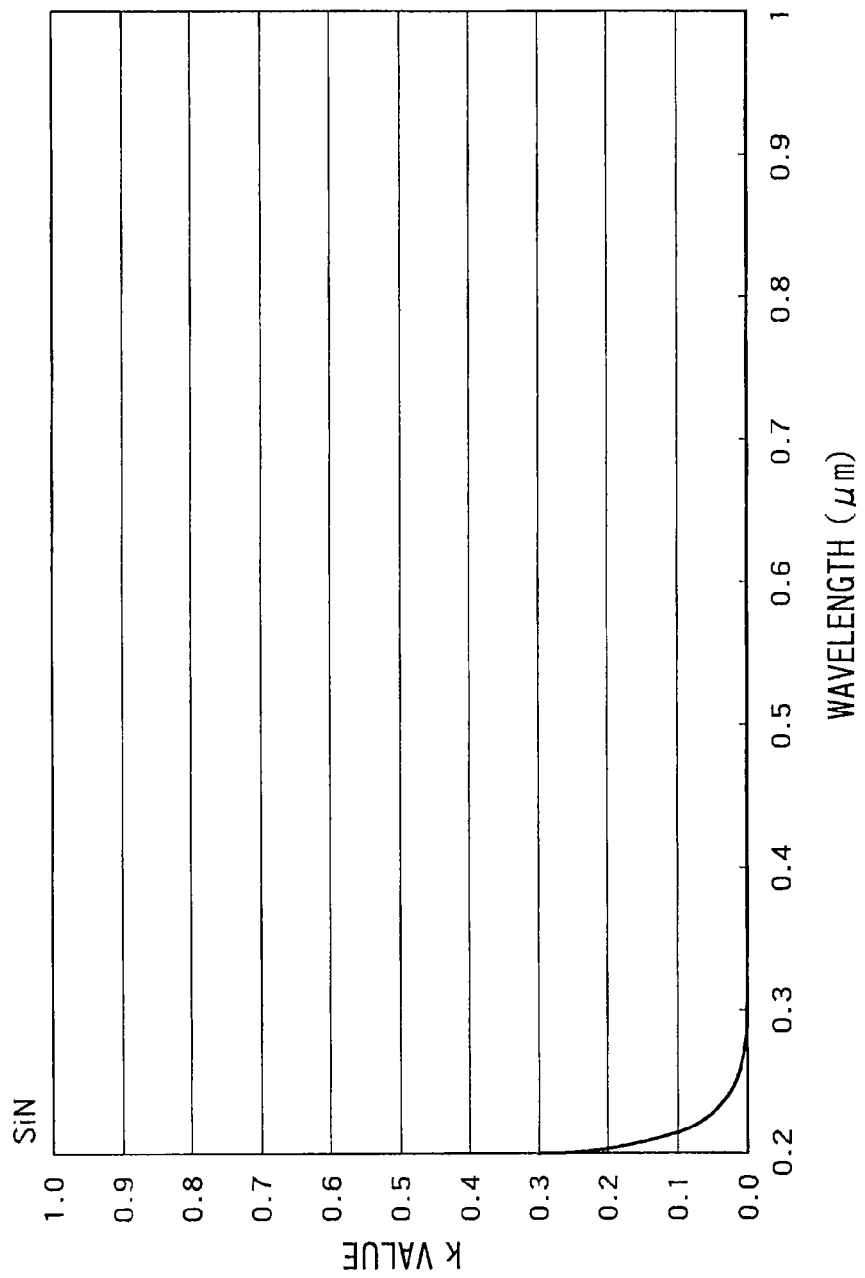
FIG. 11 is a graph showing the relation between the wavelength of an incident light and an absorption coefficient when a pattern is made of SiN.

The relation between the wavelength and the absorption coefficient k depends on the material that constitutes the pattern. For example, as shown in the graph regarding SiN in FIG. 11, there are cases where the absorption coefficient k hardly depends on the wavelength of an incident light. However, when the absorption coefficient k remarkably changes in response to the wavelength as in amorphous silicon, the position of the defect within the stacked film can be highly accurately specified.

If the thickness of the stacked film and the absorption coefficient k per wavelength are known, the amount of the light reaching each depth can be estimated. It is therefore possible to select a proper wavelength and accurately specify the position in the depth direction.

The pattern inspection apparatus according to at least one embodiment described above finds the gray value difference between the pattern image and the reference image for each of the optical conditions, and specifies the position of the defect in the depth direction from the relation of the obtained gray value difference between the optical conditions. It is therefore possible to highly accurately find the position in the depth direction regardless of the size of the defect.

(2) Pattern Inspection Method

Several embodiments of a pattern inspection method are briefly described below with reference to FIG. 12 and FIG. 13.

(a) First Embodiment

Figure 12:
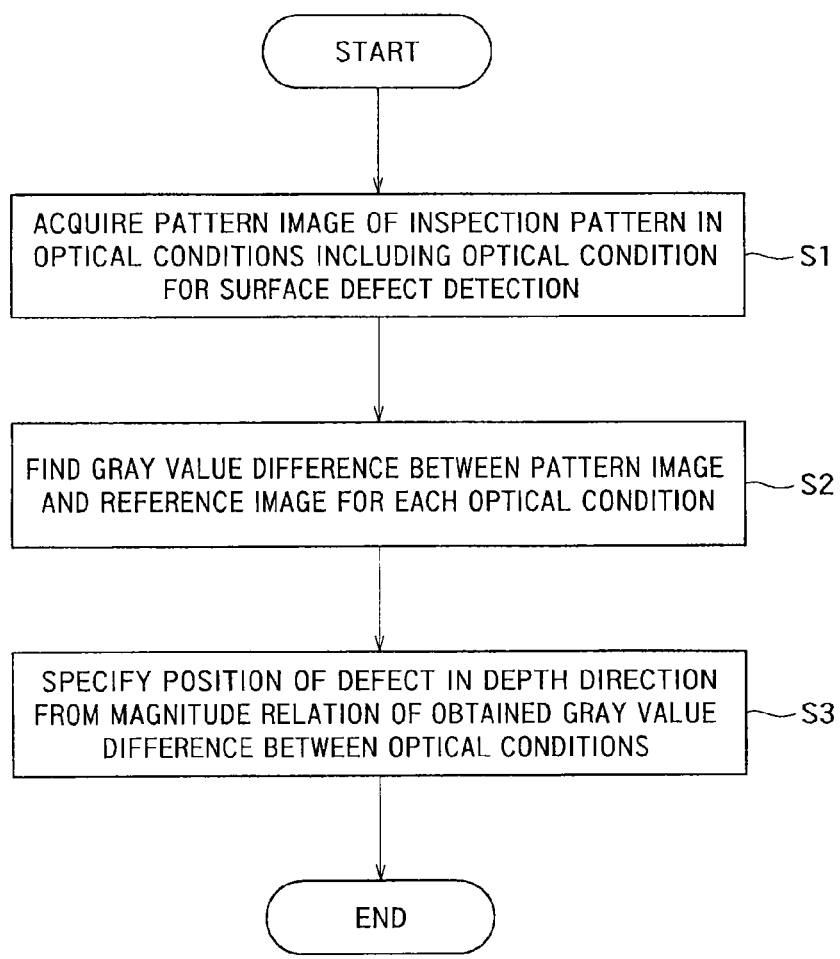
FIG. 12 is a flowchart showing a schematic procedure of a pattern inspection method according to a first embodiment.

FIG. 12 is a flowchart showing a schematic procedure of a pattern inspection method according to a first embodiment.

First, a light L1 is applied in a plurality of optical conditions to a wafer W in which an inspection target pattern P1 is formed, and a reflected light is detected to acquire each pattern image (step S1). The inspection pattern is constituted of stacked films. The optical conditions include an optical condition for detection of a defect on the surface of the stacked film.

A gray value difference between the pattern image and a reference image is then found for each of the optical conditions (step S2). Here, when the die-to-die comparison or cell-to-cell comparison is used, an image of a pattern P2 may be used as the reference image. The pattern P2 is formed by a pattern having the same design as the pattern P1, and located in a region different from the region where the pattern P1 is formed within the surface region of the wafer W. Alternatively, an image obtained regarding a reference pattern which has been previously ascertained to be nondefective, or an image obtained by a simulation may be used as the reference image.

A rough position of each defect in the depth direction is then specified from the magnitude relation of the obtained gray value difference between the optical conditions (step S3). More specifically, whether each defect is present on the surface of the stacked film or present within the stacked film is specified.

(b) Second Embodiment

Figure 13:
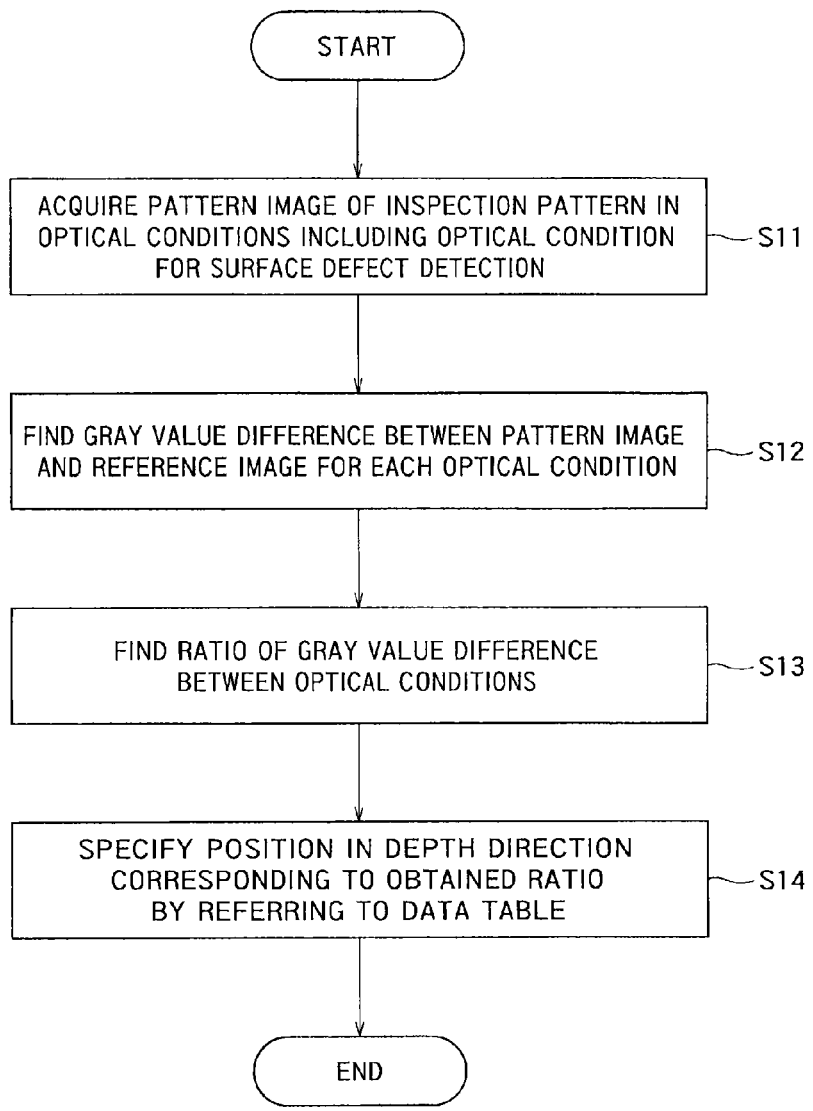
FIG. 13 is a flowchart showing a schematic procedure of a pattern inspection method according to a second embodiment.

FIG. 13 is a flowchart showing a schematic procedure of a pattern inspection method according to a second embodiment.

First, as in the first embodiment described above, a light L1 is applied in a plurality of optical conditions to a wafer W in which an inspection target pattern P1 is formed, and a reflected light is detected to acquire each pattern image (step S11). A gray value difference between the pattern image and a reference image is then found for each of the optical conditions (step S12).

The ratio of the gray value difference is then found between the optical conditions (step S13).

Finally, by referring to a prepared data table regarding the ratio of the gray value difference between the optical conditions and the position of the defect in the depth direction, the position in the depth direction corresponding to the ratio found in step S13 is specified, and outputted as an inspection result (step S14).

Thus, according to the present embodiment, the data table regarding the position of the defect in the depth direction and the ratio of the gray value difference between the optical conditions is prepared, and the ratio of the pixel gray value difference between the optical conditions found for each defect is compared with the data table. It is therefore possible to accurately calculate the position of the defect in the depth direction.

The pattern inspection method according to at least one embodiment described above finds the gray value difference between the pattern image and the reference image for each of the optical conditions, and quantitatively specifies the position of the defect in the depth direction from the relation of the obtained gray value difference between the optical conditions. It is therefore possible to highly accurately find the position in the depth direction regardless of the size of the defect.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A pattern inspection method comprising:
applying a light to a substrate under a plurality of optical conditions which are different from each other, the substrate comprising an inspection target pattern in which a stacked film is formed;
detecting a reflected light from the substrate to acquire a pattern image for each of the different optical conditions;
outputting a gray value difference between the pattern image and a reference image for each of the different optical conditions; and
specifying a position of the defect in a stacking direction of the stacked film from a relation of the obtained gray value difference between the different optical conditions,
wherein the optical conditions comprise at least one of a wavelength, a focus position, and a polarized light.

2. The method of claim 1,
wherein the relation is a magnitude relation of the gray value difference between the optical conditions.

3. The method of claim 1,
wherein the relation is a ratio of the gray value difference between the optical conditions, and
the position of the defect is specified by comparing the ratio of the gray value difference between the optical conditions with a prepared data table regarding the position of the defect in the stacking direction and the ratio of the gray value difference between the optical conditions.

4. The method of claim 1,
wherein applying the light in the optical conditions comprises applying the light to the substrate in a plurality of wavelengths different in the light absorption rate of the stacked film.

5. The method of claim 1,
wherein applying the light in the optical conditions comprises applying the light to the substrate at a plurality of focus positions.

6. The method of claim 1,
wherein applying the light in the optical conditions comprises applying a plurality of polarized lights to the substrate.

7. The method of claim 1,
wherein the optical conditions comprise optical conditions for detection of defects located at different depths within the stacked film.

8. A pattern inspection apparatus comprising:
an illumination unit configured to generate a light, and apply the light to a substrate under a plurality of optical conditions which are different from each other, the substrate comprising an inspection target pattern in which a stacked film is formed;
a detection unit configured to detect a reflected light from the substrate to output a signal;
a gray value difference output unit configured to process the signal from the detection unit to acquire a pattern image for each of the different optical conditions, and output a gray value difference between the pattern image and a reference image for each of the different optical conditions; and
a defect position specifying unit configured to specify the position of the defect in the stacking direction of the stacked film from a magnitude relation of the gray value difference between the different optical conditions,
wherein the optical conditions comprise at least one of a wavelength, a focus position, and a polarized light.

9. The apparatus of claim 8,
wherein the illumination unit illuminates the substrate in a plurality of wavelengths different in the light absorption rate of the stacked film.

10. The apparatus of claim 9,
wherein the illumination unit comprises
a single light source, a plurality of wavelength filters configured to transmit lights having different wavelengths among lights from the single light source, and
a switch located on an optical path of the lights emitted from the light source and configured to selectively switch between the wavelength filters.

11. The apparatus of claim 9,
wherein the illumination unit comprises a single light source variable in wavelength.

12. The apparatus of claim 9,
wherein the illumination unit comprises a plurality of light sources different in wavelength.

13. The apparatus of claim 12, further comprising a plurality of illumination optical systems and imaging optical systems and a plurality of detection units corresponding to the number of the light sources.

14. The apparatus of claim 9,
wherein the illumination unit comprises a single light source,
the apparatus further comprising
a splitting element configured to split the lights from the light source into a plurality of optical paths,
a plurality of wavelength filters respectively located on the optical paths and configured to allow passage of a light having a desired wavelength among the split lights,
a plurality of imaging optical systems and a plurality of detection units corresponding to the number of the optical paths, and
a plurality of illumination optical systems corresponding to the number of the optical paths, each of the illumination optical systems guiding the light which has passed through each of the wavelength filters to the substrate to illuminate the substrate, and guiding the illumination light from the substrate to each of the imaging optical systems.

15. The apparatus of claim 8, further comprising a focus position adjusting unit configured to vary the focus position of the light applied to the substrate.

16. The apparatus of claim 15, further comprising a plurality of illumination optical systems, and a plurality of imaging optical systems corresponding to the number of the illumination optical systems.

17. The apparatus of claim 8, further comprising a polarization unit configured to apply a plurality of different polarized lights to the substrate.

18. The apparatus of claim 17,
wherein the polarization unit comprises a plurality of different polarization filters, and
the apparatus further comprising
a plurality of illumination optical systems corresponding to the number of the polarization filters, and
a plurality of imaging optical systems corresponding to the number of the illumination optical systems.

19. The apparatus of claim 8,
wherein the optical conditions comprise a plurality of second optical conditions for detection of defects located at different depths within the stacked film.

20. A pattern inspection apparatus comprising:
an illumination unit configured to generate a light, and apply the light to a substrate under a plurality of optical conditions which are different from each other, the substrate comprising an inspection target pattern in which a stacked film is formed;
a detection unit configured to detect a reflected light from the substrate to output a signal;
a gray value difference output unit configured to process the signal from the detection unit to acquire a pattern image for each of the different optical conditions, and output a gray value difference between the pattern image and a reference image for each of the different optical conditions; and
a defect position specifying unit configured to specify the position of the defect in a stacking direction of the stacked film by comparing a ratio of the gray value difference of the pattern image and the reference image between the optical conditions with a data table regarding the position of the defect in the stacking direction and the ratio of the gray value difference between the different optical conditions,
wherein the optical conditions comprise at least one of a wavelength, a focus position, and a polarized light.

* * * * *